United States Patent [19]

Rogasch et al.

[11] Patent Number: 5,094,530
[45] Date of Patent: Mar. 10, 1992

[54] ATOMIC ABSORPTION SPECTROMETER

[75] Inventors: Klaus P. Rogasch, Uhldingen-Mulhofen; Rolf Tamm, Salem, both of Fed. Rep. of Germany

[73] Assignee: Bodenseewerk Perkin Elmer GmbH, Uberlingen, Fed. Rep. of Germany

[21] Appl. No.: 435,432

[22] PCT Filed: Mar. 13, 1989

[86] PCT No.: PCT/EP89/00261

§ 371 Date: Nov. 7, 1989

§ 102(e) Date: Nov. 7, 1989

[87] PCT Pub. No.: WO89/08833

PCT Pub. Date: Sep. 21, 1989

[30] Foreign Application Priority Data

Mar. 18, 1988 [DE] Fed. Rep. of Germany ....... 3809212

[51] Int. Cl.$^5$ ........................................... G01N 21/74
[52] U.S. Cl. ..................................... 356/307; 356/312
[58] Field of Search ....................... 356/307, 312, 244

[56] References Cited

U.S. PATENT DOCUMENTS 3,825,344  7/1974  Bonne ................................. 356/307

FOREIGN PATENT DOCUMENTS 1964469 10/1973 Fed. Rep. of Germany .
2148783  5/1974 Fed. Rep. of Germany .
2314207 11/1979 Fed. Rep. of Germany .
2165106  2/1984 Fed. Rep. of Germany .
3534417  4/1987 Fed. Rep. of Germany .

OTHER PUBLICATIONS

Liddel et al., *Analytical Chemistry*, vol. 52, No. 8, Jul. 1980, pp. 1256–1260.

*Primary Examiner*—F. L. Evans
*Attorney, Agent, or Firm*—Thomas P. Murphy; Edwin T. Grimes

[57] ABSTRACT

An atomic absorption spectrometer with electrothermal atomization of the sample and background compensation by use of Zeeman effect comprises a furnace (130) for the electrothermal atomization of the sample which furnace is heated transverse to the direction of propagation of the measuring light beam (18) of the atomic absorption spectrometer and a switchable solenoid (44) for generating a magnetic field at the location of the sample which magnetic field extends parallel to the direction of propagation of the measuring light beam (18) such that the longitudinal Zeeman effect is obtained with switching on the solenoid (44). The solenoid (44) has pole pieces (46,48) with aligned apertures (50,52) for the passage of the measuring light beam (18). A contact carrier (96) is arranged on the pole pieces (48,50) in which contact carrier contacts (128,176) are supported in order to hold the transversely heated furnace (130), the axes of said contacts being perpendicular to the axis of the measuring light beam (18). Field coils (60,62) are arranged directly on the pole pieces (46,48). The contact carrier (96) forms an integral element with the coil holder (56,58).

5 Claims, 9 Drawing Sheets

ATOMIC ABSORPTION SPECTROMETER

TECHNICAL FIELD

The invention relates to an atomic absorption spectrometer with electrothermal atomization of the sample and background compensation by use of the Zeeman effect.

Atomic absorption spectrometers serve for determining the amount or concentration of an element looked for in a sample. For this purpose a measuring light beam from a line emitting light source, a hollow cathode lamp for example, is directed to a photo-electrical detector. An atomizing device is arranged in the path of rays of this measuring light beam. The sample which is to be analyzed is atomized in this atomizing device such that the components of the sample are present in atomic state. The measuring light beam contains the resonant lines of the element looked for. These resonant lines of the measuring light beam are absorbed by the atoms of the element looked for in the cloud of atoms, while ideally the other elements contained in the sample do not influence the measuring light beam. Therefore the measuring light beam is subjected to an attenuation which is a measure of the number of the atoms looked for in the path of the measuring light beam and thus a measure of the concentration or the amount of the looked-for element in the sample, depending on the method of atomization applied. The absorption to which the measuring light beam is subjected is not only caused by the atoms of the element looked for. There is a "background absorption" due to the absorption of the light by molecules for example. This background absorption has to be compensated for particularly high sensitive measurements.

A flame may serve as atomizing device into which a sample is sprayed in as a solution. For high sensitive measurements the electrothermal atomization is preferably used: The sample is introduced into a furnace which is heated to high temperature by passing electrical current therethrough. Thereby the sample is dried at first, then ashed and at last atomized. Then a "cloud of atomes" is generated in the furnace in which cloud the atom looked for is present in atomic state. The measuring light beam is passed through this furnace. These furnaces can have different shapes. Conventionally they are made of graphite.

The "Zeeman effect" is used for background compensation. When a magnetic field is applied to the absorbing atoms in the atomized sample a splitting and shifting of the resonant lines of these atoms is effected. Then the resonant lines of the atoms coincident no longer with the spectral lines of the measuring light beam and no atomic absorption takes place in the borderline case. This permits discrimination between non-atomic background absorption which is also present when the magnetic field is applied, and real atomic absorption which is superposed to the background absorption when the magnetic field is not applied.

The present invention relates to an atomic absorption spectrometer in which the atomization of a sample is effected by the electrothermal atomization described and in which the Zeeman effect is used for background compensation in the way described also.

BACKGROUND ART

From German Patent Application 1,964,469 an atomic absorption spectrometer is known wherein the radiation originates from a single light source designed as a line emitter, the radiation of which passing through the sample is frequency modulated by use of the longitudinal Zeeman effect. In this prior atomic absorption spectrometer a hollow cathode lamp is arranged between the pole pieces of a solenoid. One of the pole pieces has a bore through which the measuring light beam passes. Then the measuring light beam is directed through a flame serving as atomizing device and a monochromator and impinges upon a photo-electrical detector. The solenoid is arranged to be switched on and off, whereby the atomic absorption of the sample atoms compensated with respect to the background absorption can be determined from the difference of the signals with the solenoid switched off and switched on. The windings of the solenoid are provided on the pole pieces.

In this prior art atomic absorption spectrometer the emission lines of the line emitting light source are periodically shifted by the Zeeman effect and thus the emitted light frequency is modulated and not the absorption lines of the sample. This may cause problems when a hollow cathode lamp is used as light source because the discharge of the hollow cathode lamp is influenced by the magnetic field, as already mentioned in German Patent Application 1,964,469.

From German Patent Application 2,165,106 it is known to apply the magnetic field of a solenoid arranged to be switched on and off to the atomizing device, i.e. to the sample which is to be atomized, instead to the light source. Therein the atomizing device is a flame. The magnetic field is applied perpendicular to the direction of propagation of the measuring light beam. A splitting of the absorption lines due to the "transverse" Zeeman effect is effected, which again effects a relative shift of the emission lines of the measuring light beam and the absorption lines of the sample. Again it can be discriminated between atomic absorption by the atoms of the element looked for and non-specific background absorption by switching the magnetic field on and off.

When the transverse Zeeman effect is used a spectral line is split into a central line the wave length of which corresponds to the non-shifted wave length of the respective line with the magnetic field switched off and two side lines which relative thereto are shifted to longer and shorter wave lengths. The central line and the side lines are polarized differently. Therefore the influence of the central line can be eliminated by a polarizer. Such a polarizer however causes a light loss of 50%.

Furnaces are known as atomizing devices for the electrothermal atomization of the sample. Graphite tubes serve for this purpose for example, which are held between annular contacts and through which the measuring light beam passes in longitudinal direction. A strong electrical current is passed through the annular contacts through the graphite tube. Thereby the sample introduced into the graphite tube is atomized and forms a "cloud of atoms" within the graphite tube. In this cloud of atoms the element looked for is present in atomic state. Such atomizing devices operating with a graphite tube are known from German Patent Application 23,14,207 and German Patent Application 21,48,783, for example.

It is also known to effect compensation of the background absorption by the Zeeman effect in such atomizing devices which operate with a graphite tube flown through by current in longitudinal direction. For this purpose a alternating magnetic field directed transverse to the direction of propagation of the measuring light beam is applied to the graphite tube by a solenoid. Thereby the transverse Zeeman effect is caused as well, whereby a polarizer in the path of rays is required.

Furnaces for the electrothermal atomization of a sample in an atomic absorption spectrometer are known in which the current is not passed through a graphite tube in longitudinal direction but in circumferential direction. Examples for this are U.S. Pat. No. 4,407,582 and German patent application 35,34,417 as well as the publication in "Analytical Chemistry" 58 (1986), 1973 having substantially the same contents.

A contact arrangement provided with two contacts for the current supply to a transversely heated tubular furance for the electrothermal atomization in atomic absorption spectroscopy is known from not pre-published German patent application P 37,26,533.4 in which contact arrangement the furnace has longitudinal diametrically opposite contact ribs. The contacts of this contact arrangement the axes of which extend perpendicular to the axis of the furnace and to the direction of propagation of the measuring light beam, form a cavity under operational conditions in which the tubular furnace is accomodated. There the furnace is held between v-shaped grooves of the contacts. The cavity is formed substantially by an impression in one of the contacts which is closed by the other contact except for a partion gap. Inert gas passages open into the grooves.

A tubular furnace for the electrothermal atomization of samples in atomic absorption spectroscopy is known from not pre-published German patent application P 37,35,013.7. This furnace comprises a tubular furnace body with contact sockets arranged on opposite sides. The contact sockets have contact ribs extending longitudinally to the tubular proper furnace body adjacent to which are cylindrical contact pieces with conical contact surfaces. These contact ribs have contractions. According to German patent application P 37,35,013.7 these contractions are formed by cylindrical turned out portions. An equal temperature along the furnace body shall be achieved by this design. The contact arangement is similar to that in German patent application P 37,26,533.4 mentioned heretofore.

DISCLOSURE OF THE INVENTION

It is the object of the invention to improve the useful signal in the atomic absorption spectrometer of above mentioned type.

A further object of the invention is to achieve a more uniform temperature distribution along the furnace body in the atomic absorption spectrometer of the type heretofore than this is possible with prior "Zeeman'-'—atomic absorption—spectrometers.

According to the invention this object is achieved by the combination
(a) of a furnace for the electrothermal atomization of the sample which furnace is heated transverse to the direction of propagation of the measuring light beam of the atomic absorption spectrometer, and
(b) a switchable solenoid for generating a magnetic field at the location of the sample which magnetic field extends parallel to the direction of propagation of the measuring light beam such that the longitudinal Zeeman effect is obtained with the solenoid switched on.

Current is supplied to the graphite tube transverse to the direction of the measuring light beam. Thereby a more uniform temperature distribution is achieved. Nevertheless one side of the graphite tube remains free for the supply of the sample because the magnetic field is generated in the direction of propagation of the measuring light beam.

A further advantage of this arrangement is that the longitudinal Zeeman effect is obtained at the sample, that means splitting of the absorption line without a central line having the original wavelength is effected. Therefore it is not necessary to eliminate such a central line by a polarizer in the path of rays. Thereby the useful signal is improved.

Furthermore the possibility is offered that
(a) in addition to a line emitting first light source generating the measuring light beam a second light source emitting a continuum is provided for background compensation and is switched on alternately with the line emitting first light source, and
(b) a beam splitter is optionally movable into the path of rays and is arranged such that a measuring light beam originating from a second light source is reflected into the path of rays of the measuring light beam.

Further embodiments of the invention are subject matter of the sub-claims.

An embodiment of the invention will now be described in further detail with reference to the accompanying drawings.

PREFERRED EMBODIMENT OF THE INVENTION

Figure 1:
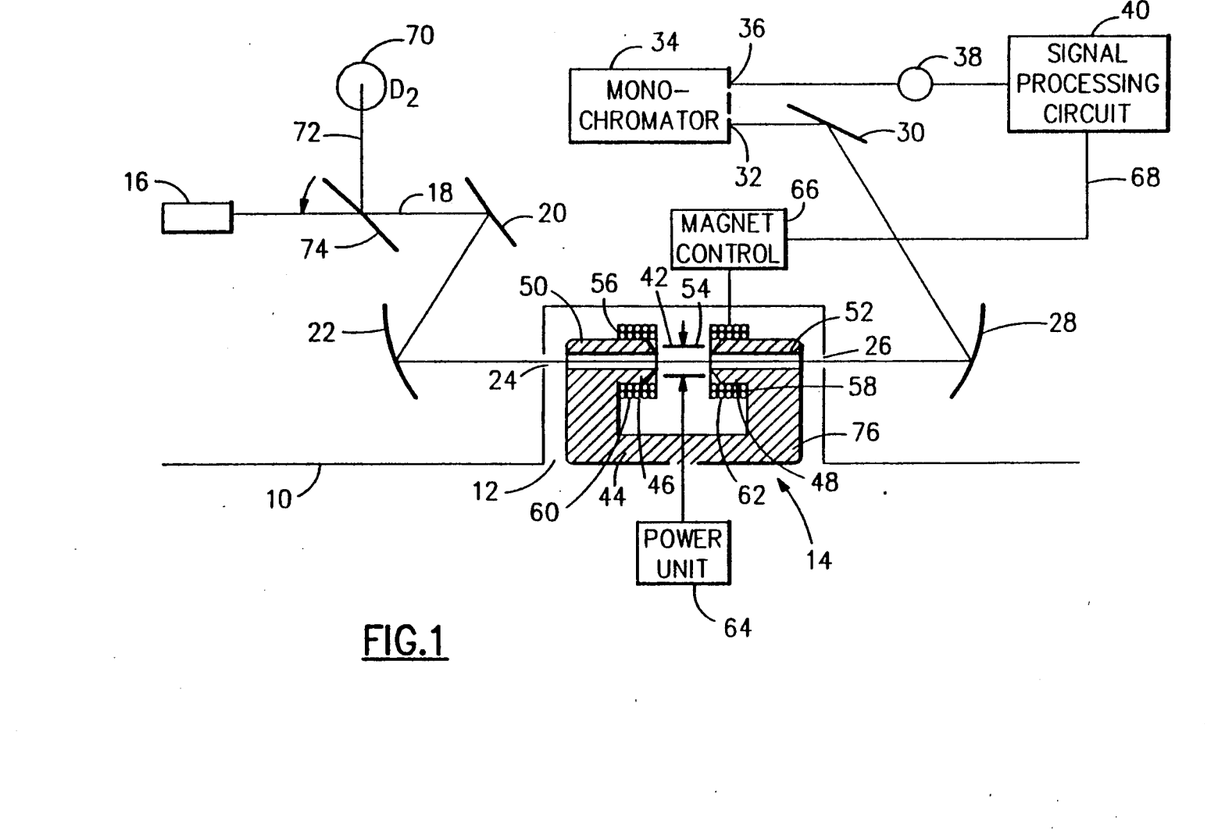
FIG. 1 shows shematically the construction of an atomic absorption spectrometer in which the background compensation is compensated by use of the longitudinal Zeeman effect.

The Figure shows a schematical illustration of the entire atomic absorption spectrometer.

The atomic absorption spectrometer has a housing 10 in which the lamps, the optical system and the photosensitive detector are arranged. The housing defines a sample cavity 12. An atomizing device is arranged in the sample cavity 12.

The atomic absorption spectrometer has a hollow cathode lamp as first light source 16. The light source 16 emitts a line spectrum which corresponds to the resonant lines of a certain element looked for. A measuring light beam 18 originates from the light source 16. The measuring light beam 18 is deviated by a plane mirror 20 and collected in the center of the sample cavity by a concave mirror 22 through an opening 24 of the housing 10. Then the measuring light beam passes through an opening 26 of the housing 10 aligned with the opening 24 and impinges upon a second concave mirror 28. The second concave mirror 28 focusses the measuring light beam 18 through a plane mirror 30 on the inlet slit 32 of a monochromator 34. A photo-electrical detector 38 is arranged behind an outlet slit 36 of the monochromator 34. The signal of the photo-electrical detector 38 is supplied to a signal processing circuit 40.

The atomizing device 14 comprises a furnace for electrothermal atomization, only the actual furnace body 42 of the furnace device being illustrated in FIG. 1, and a solenoid 44 which is arranged to be switched on and off in order to generate a magnetic field at the location of the sample. The solenoid 44 has two aligned pole pieces 44 and 46 between which the furnace body 42 is arranged. Aligned bores 50 and 52 are provided in the pole pieces 46 and 48. The bores 50 and 52 are aligned with a longitudinal bore 54 of the furnace body 42. The measuring light beam 18 passes through the bores 50 and 52 and through the longitudinal bore of the furnace body. Coil holders 56 and 58, respectively, are arranged on the pole pieces 50 and 52. Coils 60 and 62, respectively, of the solenoid 44 are wound on these coil holders 56 and 58. Numeral 64 designates a power unit which controls the current through the furnace body 42. As indicated the current is supplied transversely to the direction of the measuring light beam 18 and flows through the tubular furnace body 42 in circumferential direction. The solenoid 44 is controlled by a magnet control 66 such that the magnetic field alternately is switched on and off. At the location of the sample the magnetic field of the solenoid 44 is directed within the furnace body in the direction of propagation of the measuring light beam 18. Therefore the longitudinal Zeeman effect is generated at the sample atoms when the magnetic field is switched on. That means that the absorption lines of the sample atoms are split into two lines, each, which are shifted relative to the undisturbed original absorption line. There is no atomic absorption in the sample with the wave length of the original absorption line. Therefore also the atoms of the elements looked for do not absorb the measuring light beam 18 because this measuring light beam contains only the non-shifted resonant lines which are characteristic for the element. Therefore only the background absorption is measured when the magnetic field is switched on. The portion of real atomic absorption corrected with respect to the background absorption can be determined from the measurements with the magnetic field switched on and off. For this purpose the cycle of switching the solenoid 44 on and off is supplied to the signal evaluation circuit 40 as indicated by a line 68. By using the longitudinal Zeeman effect a polarizer arranged in the path of rays can be omitted and the useful signal is improved.

A second light source 70 emitting a continuum is arranged in the housing 10. This second light source is a deuterium lamp. The second light source 70 emits a light beam 72. This light beam 72 from the second light source 70 can be deflected into the path of rays of the measuring light beam 18 through a beam splitter 74 which optionaly is movable into the path of rays of the measuring light beam 18. The first and the second light source 16 and 70, respectively, are arranged to be switched on alternately in a quick sequence such that a measuring light beam 18 with a line spectrum from the first light source (hollow cathode lamp) 16 or a measuring light beam with a continuum from the second light source (deuterium lamp) passes alternately through the cloud of atoms generated in the furnace body. In this mode of operation with the beam splitter 74 moved into the path of rays the solenoid is switched off. Then the background absorption can be determined in that the absorption of the very narrow spectral line of the first light source and the absorption of a band of continuum radiation, which is relatively wide compared to the spectral line, determined by the monochromator 34, is measured. The change between the first light source 16 and the second light source 70 is made at a frequency of more than 500 cycles per second, namely 1000 cycles per second. The way of operating with a second light source emitting a continuum as reference light source permits detection of relatively quick changes of the background absorption which could not be detected by using the Zeeman effect by means of the solenoid 44. The solenoid 44 is relatively sluggish such that the frequency of the change between atomic absorption measurement and background measurement is limited. By application of the longitudinal Zeeman effect no polarizer is required in the path of rays. Therefore the atomic absorption spectrometer can operate with a second light source 70 emitting a continuum without causing double attenuation of the light by the polarizer and additionally by the beam splitter 74, the solenoid being switched off.

Figure 2:
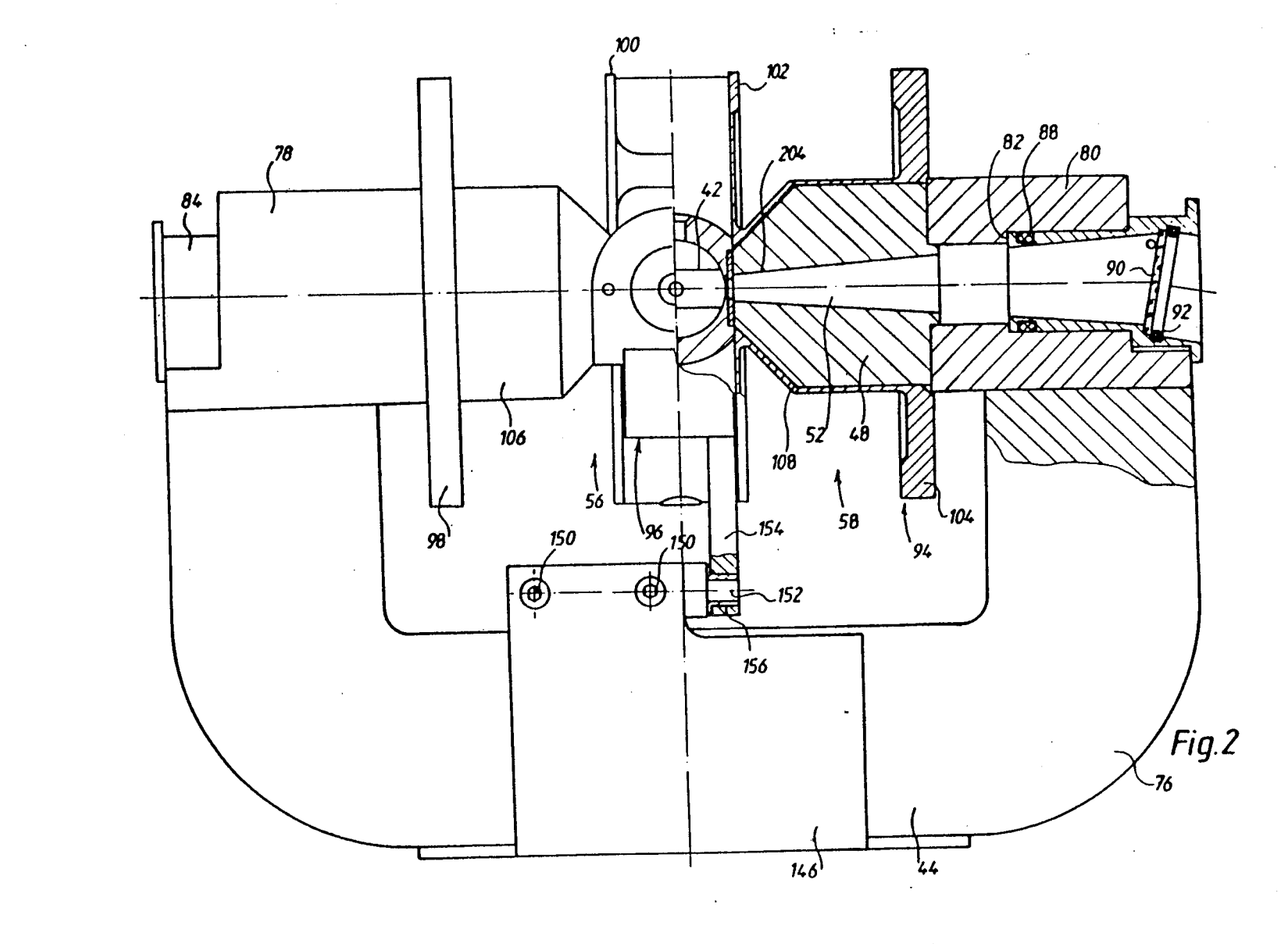
FIG. 2 shows a partially sectional side elevation of the solenoid by which the longitudinal Zeeman effect is generated and a furnace for the electrothermal atomization of a sample in the air gap of the solenoid.
Figure 3:
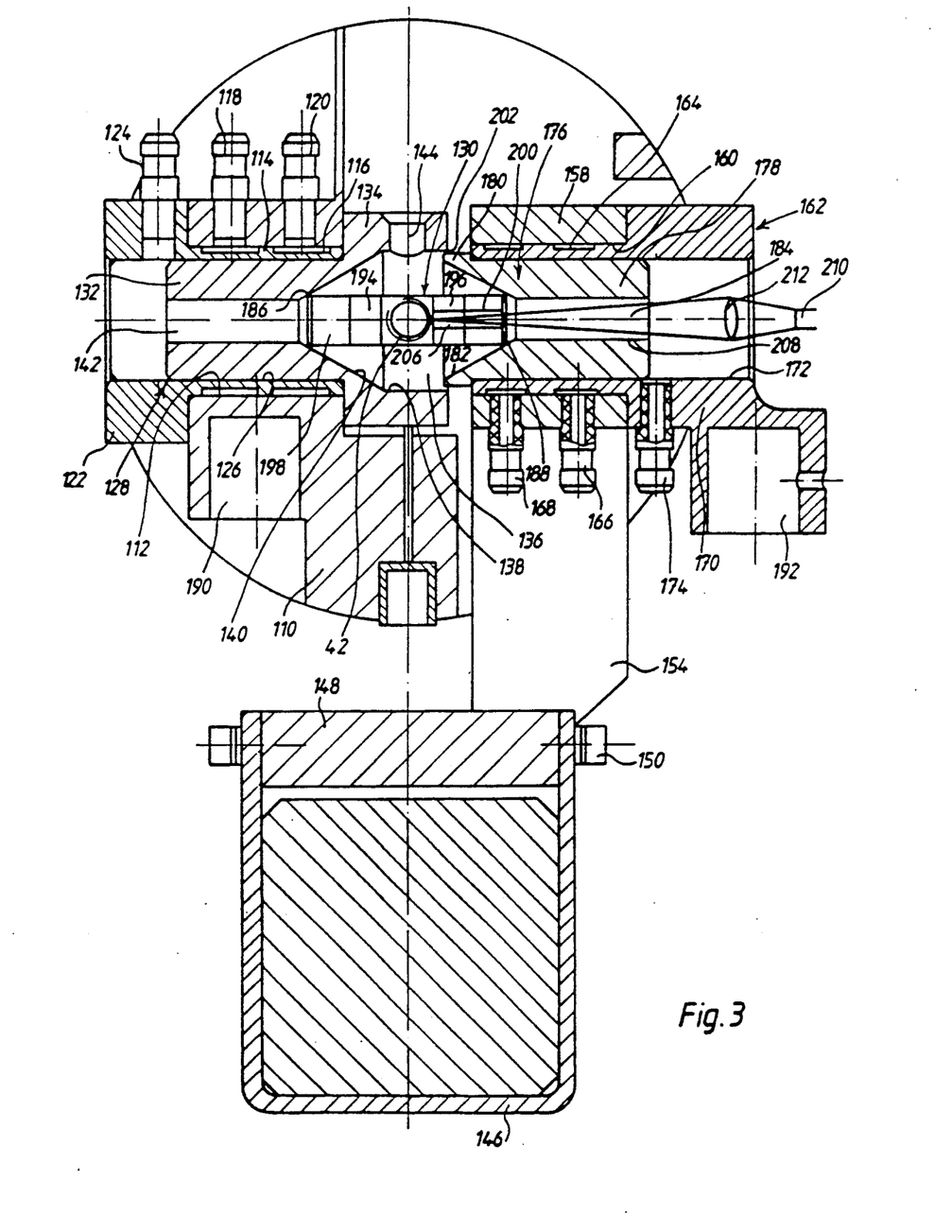
FIG. 3 shows a sectional view taken along the line III—III of FIG. 2.
Figure 4:
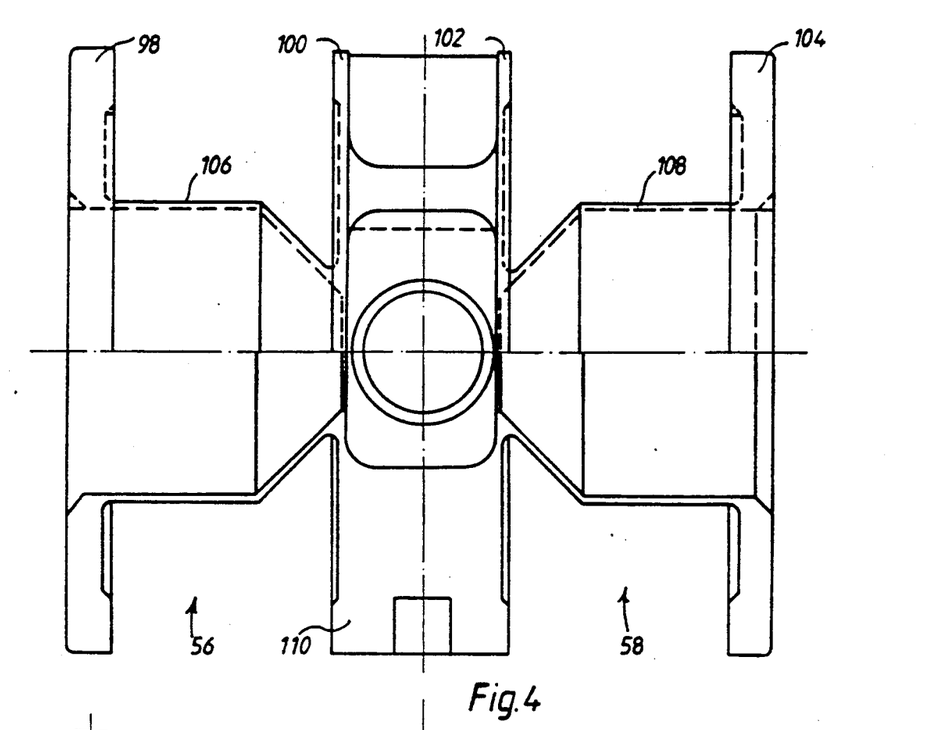
FIG. 4 shows separately a contact carrier which carries one of the contacts for holding the furnace and for the current supply to the furnace, and the coil holder forming an integral element with the contact carrier in a side elevation similar to FIG. 2.
Figure 5:
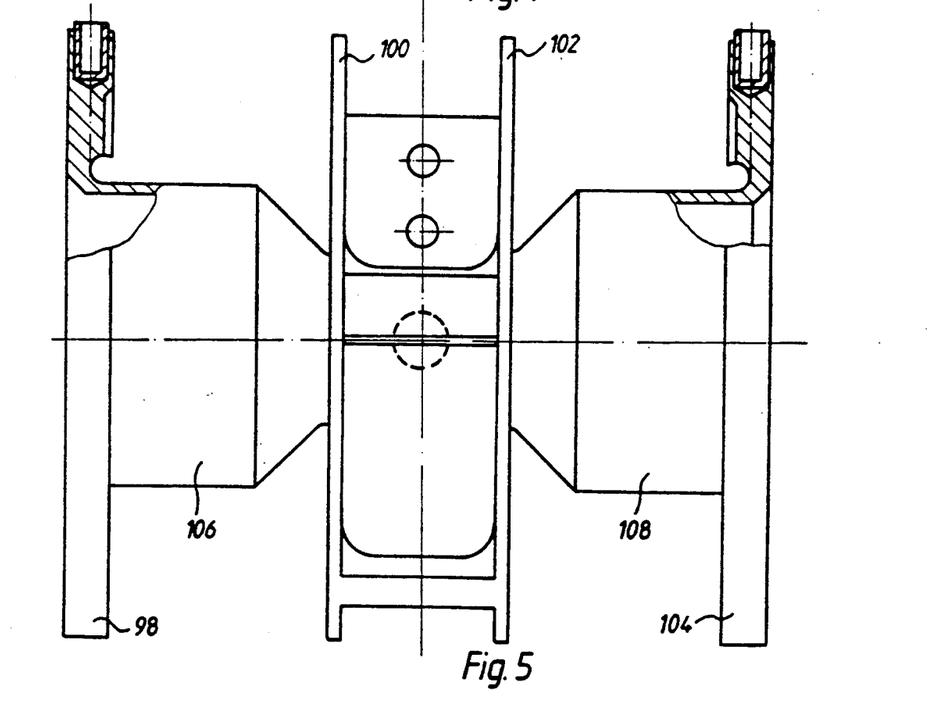
FIG. 5 shows a plan view of the element of FIG. 4.

The construction of the atomizing device with the solenoid 44 and the furnace is illustrated in detail in FIG. 2 and FIG. 3.

The solenoid 44 has a u-shaped magnetical return path 76 made of laminated iron and aligned pole pieces 46, 48. The pole pieces are cylindrical and are frustro conically tapered at the ends facing each other. The pole pieces 46 and 48 are arranged on the aligned end pieces 78 and 80, respectively, which are provided on the legs of the u-shaped magnetical return path 76 and project inwardly from there. The aligned cutouts 50 and 52, respectively, extend through the pole pieces 46 and 48 and the end pieces 78 and 80. The cutouts 50 and 52, respectively, are provided by conical inner surfaces in order to ensure focussing the measuring light beam in the center of the furnace body 42. In the area of the ends pieces 78 and 80 the cutouts 50 and 52, respectively, form shoulders 82. Window holders 84 and 86, respectively, are inserted into the cutouts 50 and 52 and are sealed by O-rings 88. Windows 90 are located in the window holders 84 and 86 which are arranged transverse in the window holders 84 and 86, respectively, in order to avoid reflections, and which are held by sealing rings 92.

An integral element 94 made of a non-magnetic material as aluminum is provided on the pole pieces 46 and 48. This element formes the coil holder 56 and 58 on which the field coils 60 and 62, respectively, are wound, and on the other hand forms a contact carrier 96 which carries one of the contacts between which the furnace is held. The field coils 60 and 62 are not illustrated in FIG. 2 and FIG. 3 for clarity.

The coil holders 56 and 58 are formed by spool-shaped elements with two flanges 98 and 100 or 102 and 104, respectively, and hub portions 106 and 108, respectively. The hub portions 106 and 108 are adapted to the shape of the pole pieces 46 and 48, respectively. A block 110 having a bore 112 is arranged between the flanges 100 and 102 facing each other of the two coil holders 56 and 58. An insert 114 is provided in the bore 112 which insert has a meander-shaped groove 116 on its outer surface which groove together with the inner surface of the bore 112 form a cooling passage. This cooling passage communicates with an inlet 118 and an outlet 120 for the cooling liquid. The insert has a head portion 122 whereon an inert gas inlet 124 is provided. A central axial bore 126 extends throughout the insert which is closed at its left end in FIG. 3. A contact 128 is provided in this axial bore by which contact a furnace 130 is held on one side for the electrothermal atomization, and through which contact also the current supply for the furnace is accomplished.

The contact has a shaft 132 which is located in the axial bore 126, and a head 134. The head 134 has a recess 136 in its end face. First of all this recess 136 is cylindrical in a section 138 adjacent to the end face and then narrows conically in a section 140. A central axial bore 142 extends in the shaft 132 and ends on the bottom of the recess 136. A radial inlet port 144 is formed in the cylindrical section 138 in the head 134 on top in FIG. 3 through which port a sample can be introduced into the furnace.

The magnetic return path 76 of the solenoid 44 is surrounded by a sheet metal element 146 having a u-shaped cross-section in which a bearing element is held by a bolt 150. A pivotable arm 154 is pivotably mounted on a pin 152 of the bearing element 152 through a bearing bushing 156. A movable block 158 is provided at the pivotable arm 154. Similar to the block 110 the block 158 has a bore 160. An insert 162 similar to the insert 114 is arranged in the bore 160. The insert 162 has meander-shaped grooves 164 on its outer surface which grooves together with the inner surface of the bore 160 form a cooling passage. This cooling passage communicates at its ends with an inlet port 166 and an outlet port 168 for the cooling liquid. The insert has a head 170. A central axial bore 172 extends through the insert 162 and the head 170. On the right side of FIG. 3 the axial bore 172 is closed by a window. An inert gas port 174 opens into the axial bore 172. A contact 176 is arranged in the axial bore 172. The contact 176 has a cylindrical shaft 178 and a flat head 180. A conical recess 182 is formed in the end face of the head 180. The recess corresponds approximately to the recess section 140. A central axial bore 184 similar to the bore 142, extends through the shaft 178 of the contact 176.

In operational position of the pivotable arm 154, as illustrated in FIG. 3, the furnace 130 is held between the contacts 128 and 176 with conical contact surfaces 186 and 188. Then the contacts 128 and 176 are aligned. The current is supplied to the furnace 130 through the blocks 110 and 158, the inserts 114 and 162 and the contacts 128 and 176. For this purpose the block 110 and the insert 162 are provided with plug-type connectors 190 and 192, respectively, for the high-current cables.

The furnace 130 contains the actual furnace body 42 which can be recognized best in FIG. 2. Diametrically opposite contact ribs 194 and 196 which can be seen in FIG. 3 extend along the furnace body 42. Substantially cylindrical contact pieces 198 and 200 are adjacent to the contact ribs 194 and 196, said contact pieces are held between the contacts 128 and 176 by the conical contact surfaces 186 and 188. The axes of the contact pieces 198 and 200 are aligned with the axes of the contacts 128 and 176 in the paper plane of FIG. 3 and extend perpendicular to the axis of the furnace body wich is aligned with the measuring light beam 18. An inlet port is provided in the furnace body perpendicular to these two axes, that means on the top of FIG. 2 and FIG. 3, which inlet port is aligned with the inlet port 144 and through which inlet port sample can be introduced into the furnace 130.

The contacts 128 and 176 form a cavity with their recesses 136 and 168 which cavity contains the furnace 130. The contacts 128 and 176 are separated from each other only by a relatively narrow separating gap 202. The pivotable arm 154 can be deflected clockwise in FIG. 3 by a pneumatic tilting device (not illustrated). This is indicated in FIG. 3 by an arrow. Thereby the block 158 with the insert 162 and the contact 176 is deflected and the furnace 130 is accessible. In this way an exchange of the furnace 130 can be accomplished. An inert gas is supplied through the inert gas ports 124 and 174. This inert gas flows through the bores 126 and 172, respectively, and the axial bores 142 and 184, respectively, to the contact pieces 198 and 200, respectively, of the furnace 130. Then the inert gas is distributed in the furnace 130 by passages which still have to be described. The contacts 128 and 176 and the furnace 130 are made of graphite. The inert gas prevents the furnace 130 from getting into contact with air oxygen, when it is heated, and thus from burning.

A shielding disc 204 with a central aperture for the measuring light beam is arranged between the contact 128 and the end face of the pole piece 48 as can be seen in FIG. 2. The shielding disc 204 is made of pyrolytic plastic with a high heat conductivity in the plane of the shielding disc 204 and a low heat conductivity perpendicular to this plane. In this way the pole piece 48 is protected from high temperatures of the furnace 130 and the contact 128.

The axial bores 172 and 184 in the insert 162 and the contact 176 and the insert gas passage 206 in the contact piece 200 and the contact ledge 196 serve simultaneously for accommodating a pyrometer path of rays 208 in which a part of the wall of the furnace element 42 is observed by a radiation detector 210 by means of an imaging system 212. The signal of the radiation detector provides a measure of the temperature of the furnace element 42 and allows control of the furnace temperature.

Figure 6:
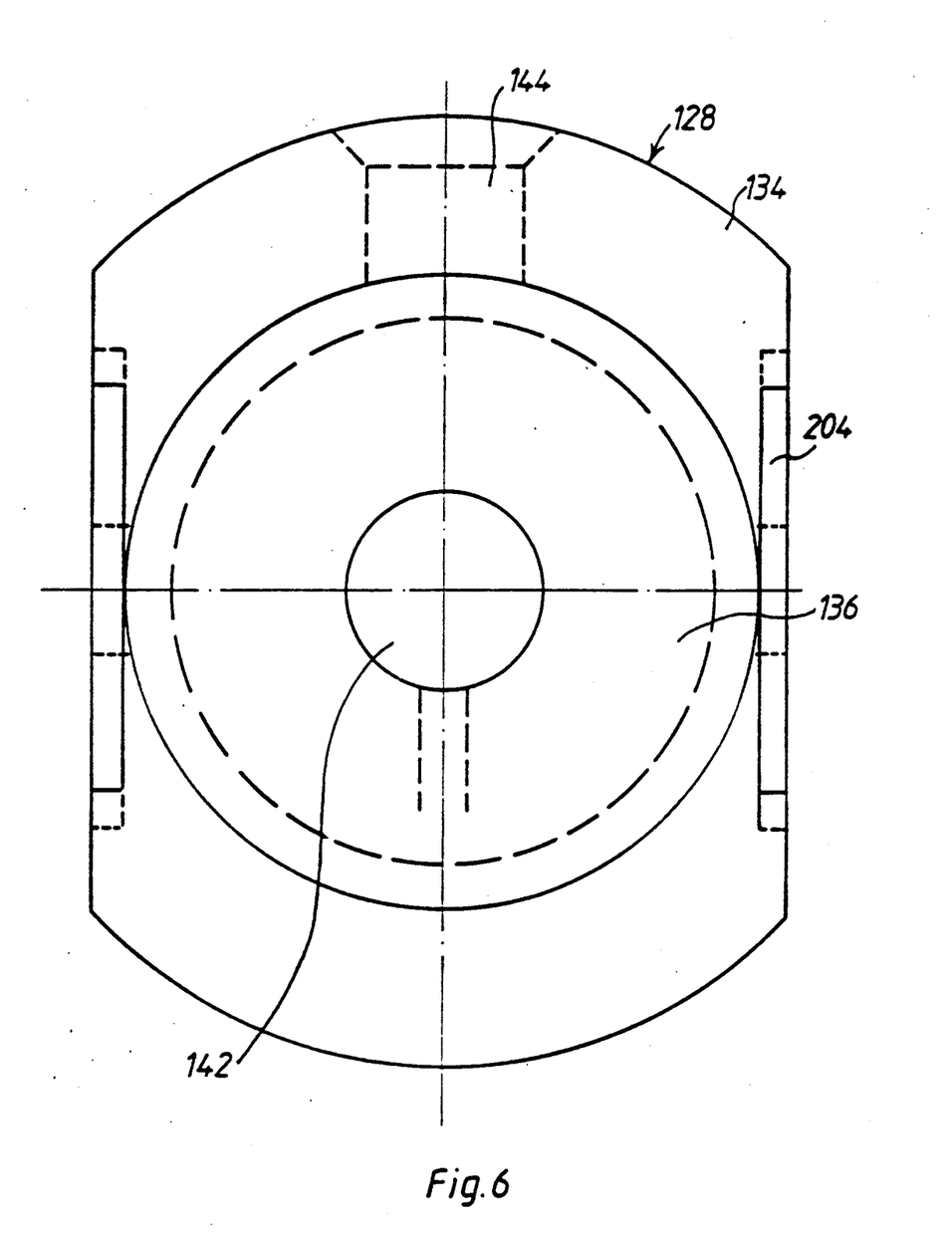
FIG. 6 shows a view of a contact similar to that of FIG. 2 by which contact the furnace is held on one side.
Figure 7:
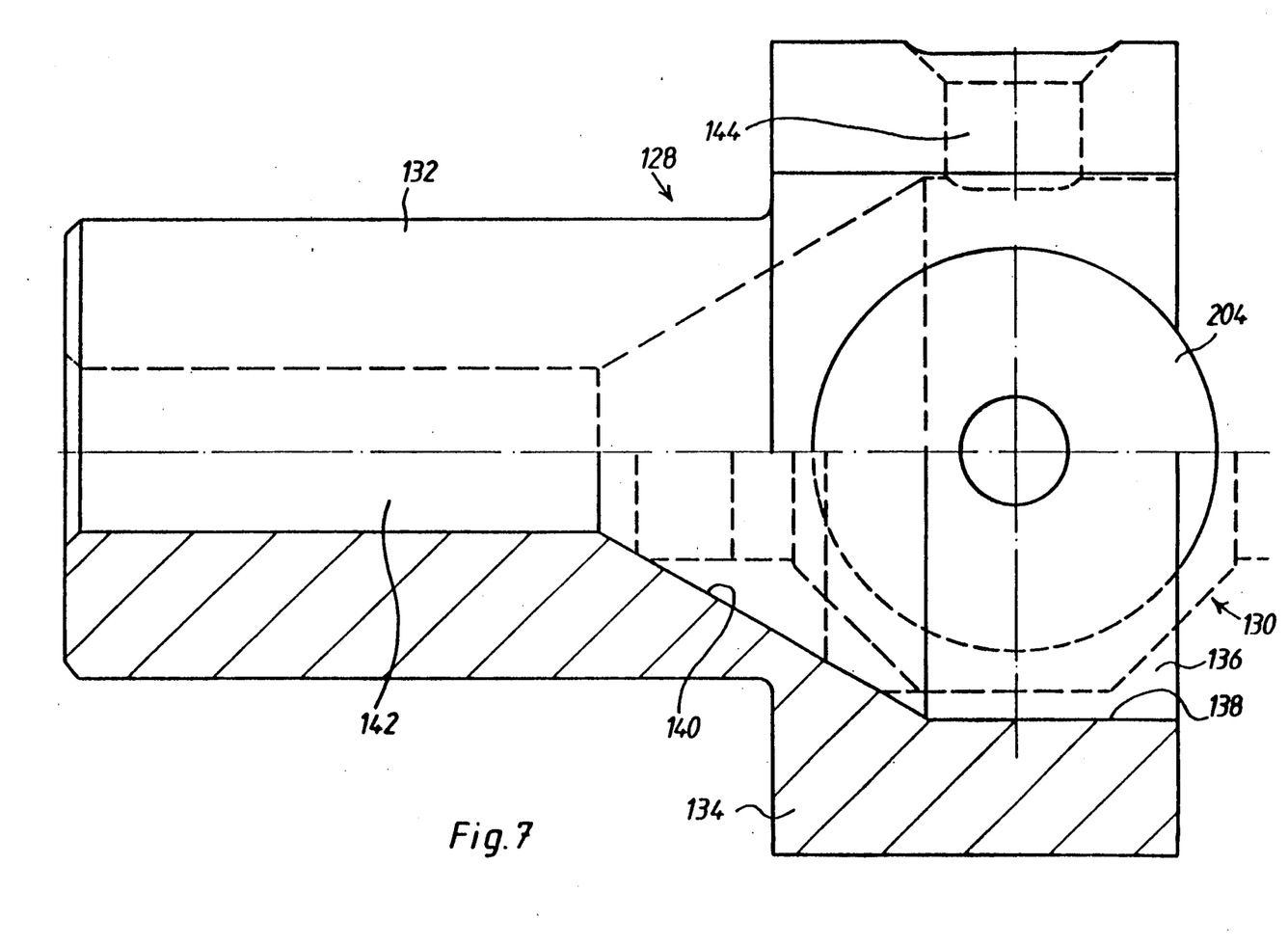
FIG. 7 shows a sectional view taken along the line VII—VII of FIG. 6.
Figure 8:
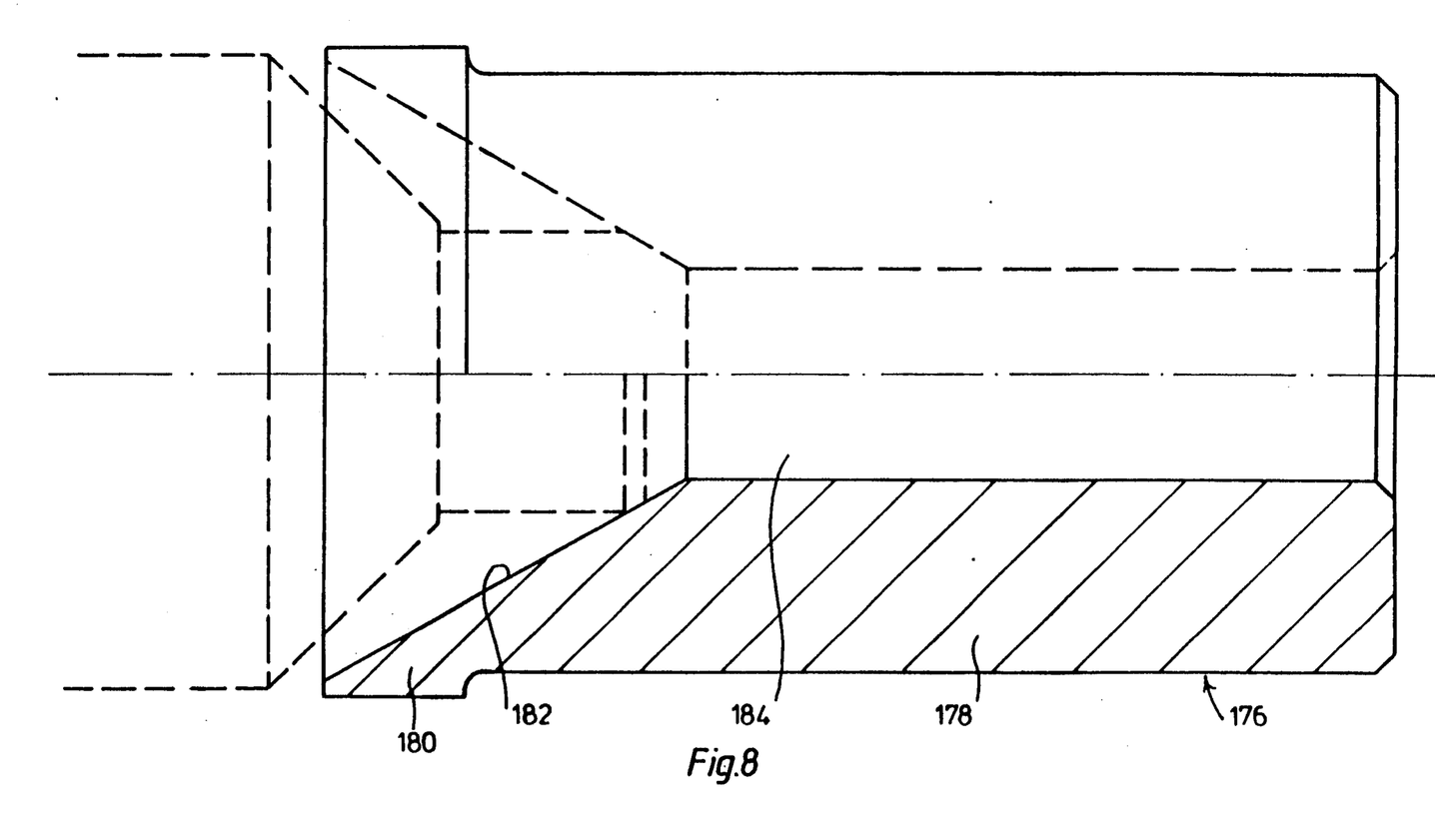
FIG. 8 shows the opposite contact in a view similar to FIG. 6.

FIG. 6 and FIG. 7 show the contact 128 with the shielding disc 204. FIG. 8 shows the opposite contact.

Figure 9:
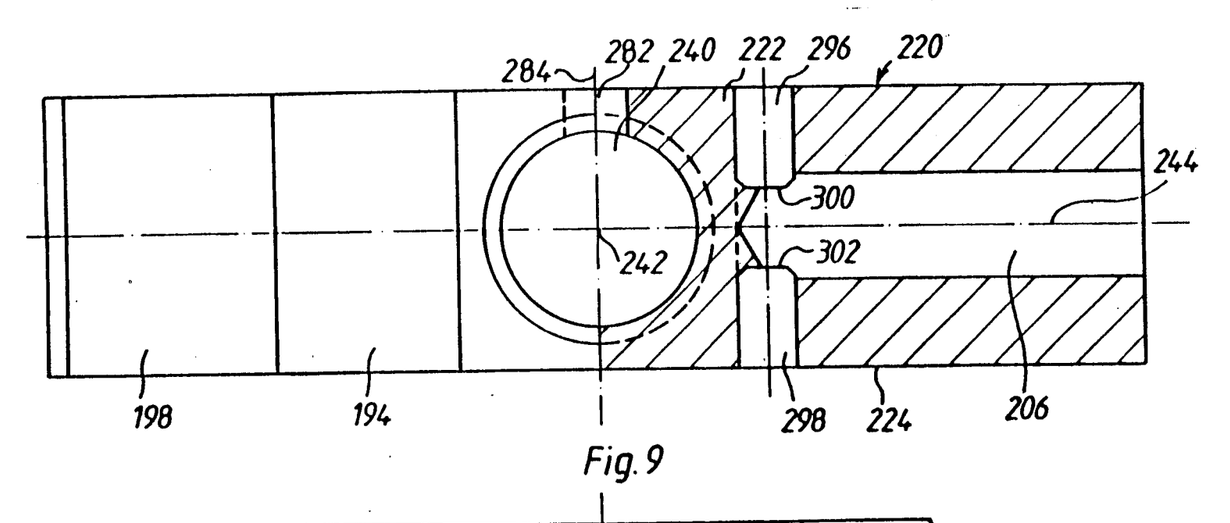
FIG. 9 shows only a partially sectional view similar to FIG. 3 of a furnace for the electrothermal atomization of the sample in the atomic absorption spectrometer of FIG. 1 to FIG. 3.
Figure 10:
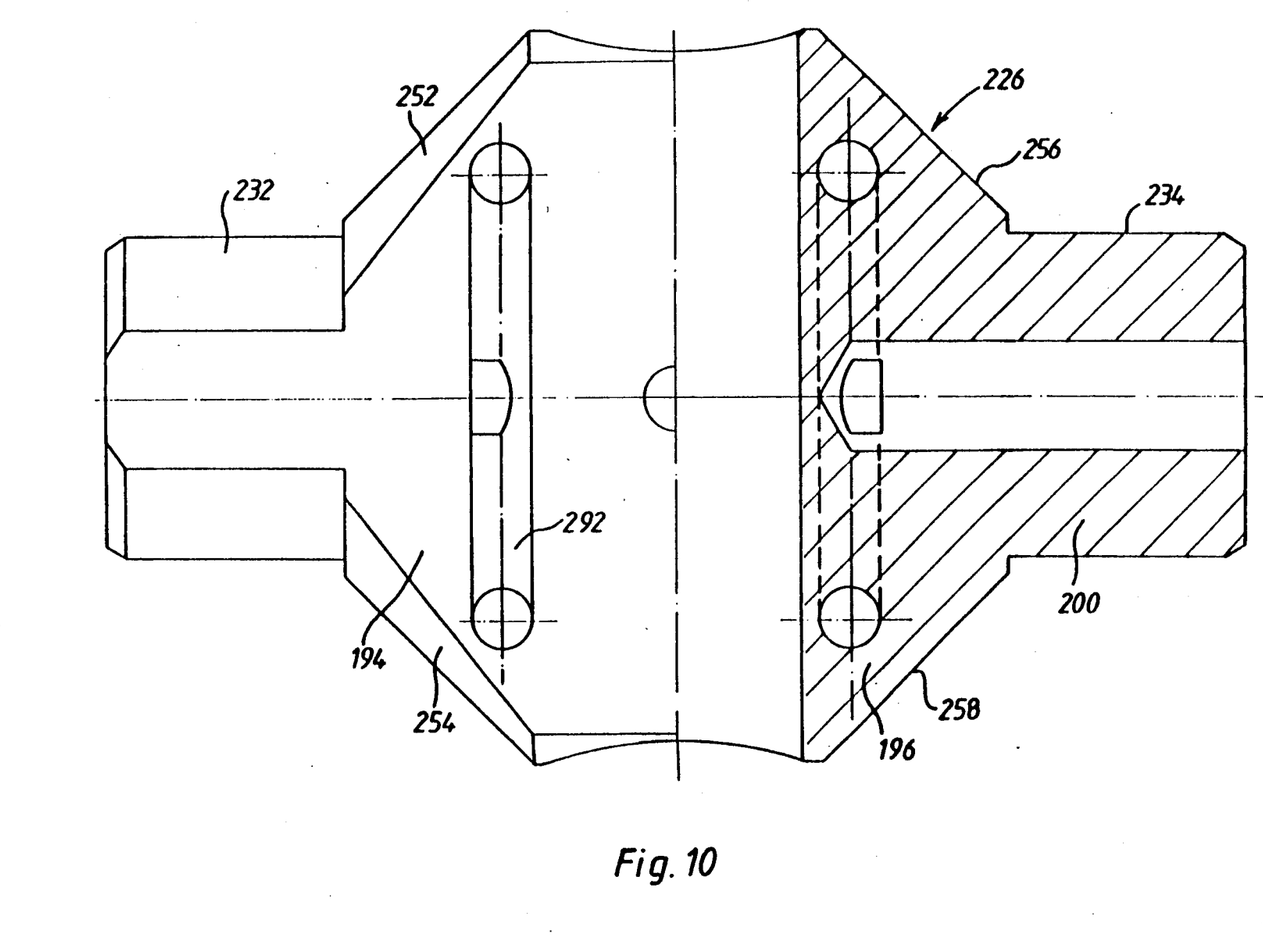
FIG. 10 shows a plan view of the furnace of FIG. 9.
Figure 11:
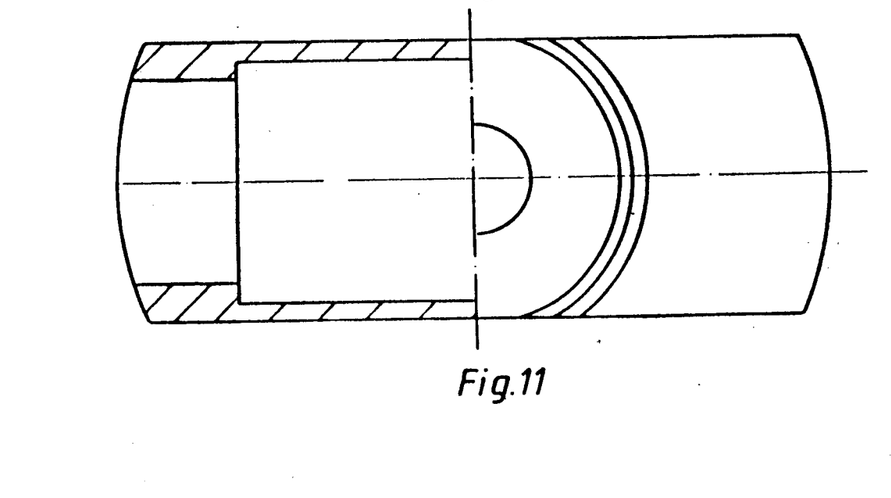
FIG. 11 shows a partially sectional view of the furnace as viewed from the left side in FIG. 9.

In FIG. 9 to FIG. 11 the furnace 130 is illustrated in detail.

In the furnace of FIG. 9 to FIG. 11 numeral 220 designates a graphite piece which forms generally a plate with an upper planar surface 222 and a lower planar surface 224. The graphite piece 220 has a center portion 226 which has generally the shape of a regular octaeder in plan view. Necks are arranged on two diametrically opposite sides of this octaeder and form the contact pieces 198 and 200. This contact pieces 198 and 200 form cylindrical surface planes 232 and 234, respectively, but are limited on the bottom and on the upper side by planar surfaces 222 and 224 and are flattend thereby. The contact pieces 198 and 200 are provided by the conical contact surfaces 186 and 188, respectively. The furnace 130 is held by these contact surfaces 186 and 188 between the contacts 128 and 176 on the side of the instrument the current being supplied through these contacts.

The sides of the octaeder perpendicular to the sides with the contact pieces 198, 200 communicate through a bore 240. The axis 242 of the bore 240 extends perpendicular to the axis 244 of the contact pieces. The part of the center portion 226 between the sides communicating through the bore 240 forms the furnace body 42.

The contact ribs 194 and 196 are adjacent to the furnace body on both sides. The contact ribs 194 and 196 are trapezoidal in the plan view of FIG. 10. The contact ribs 194 and 196 are limtied at the bottom and at the top by the planar surfaces 222 and 224 and on the sides by inclined lateral surfaces 252, 254 and 256, 258, respectively. The long parallel side of each trapezoid is adjacent to the furnace body 42. The short parallel side of each trapezoid is the side of the octaeder mentioned first and carries the contact pieces 198 or 200, respectively. The contact ribs 194 and 196 have areas of a reduced cross-section.

In the furnace according to FIG. 9 to FIG. 10 the cross-section for the power supply is reduced along the central area of the furnace body 42 by recesses 292 and 296 and 298 in the planar surfaces 222 and 224. The recesses are parallel to the axis 242 of the furnace body 42 and end at a distance from the lateral surfaces 252, 254 and 256, 258, respectively. As can be seen from FIG. 9 the recesses, 296 and 298 for example, are intersected by the insert gas passages, 206 for example. Therefore the inert gas flowing through the inert gas passages passes through apertures 300 and 302 into the recesses 296 and 298 and emerges through these apertures on both sides and along the entire furnace body 42.

The inert gas passages 206 extend in the contact pieces 198 and 200 along the axis 244. The inert gas passages extend up to the center portion 226. When inert gas is supplied from the contacts 128 and 176 on the side of the instrument through the insert gas passages 206 this inert gas is distributed through the recesses 296, 298 and flows around the furnace 130 from all sides. Thereby the furnace is prevented from air contact and thus from burning at the high atomizing temperatures.

A particularly uniform temperature distribution is achieved by reducing the cross-section for the power supply in the central area of the furnace body 42.

The furnace body 42 has an inlet port 282 through which a sample which is to be analyzed can be introduced into the furnace. The axis 284 of the inlet port 282 is perpendicular to the axes 242 and 244 of the furnace body 42 and the contact pieces 198, 200.

We claim:
1. Atomic absorption spectrometer with electrothermal atomization of a sample and background compensation by use of the Zeeman effect, comprising
   (a) a furnace for the electrothermal atomization of the sample which furnace is heated transverse to the direction of propagation of a measuring light beam of the atomic absorption spectrometer,
   (b) a switchable solenoid for generating a magnetic field at the location of the sample which magnetic field extends parallel to the direction of propagation of the measuring light beam such that the longitudinal Zeeman effect is obtained with the solenoid switched on,
   (c) the solenoid for generating the magnetic field having pole pieces with aligned apertures for the passages of the measuring light beam,
   (d) said solenoid including an air gap
   (e) a contact carrier arranged on the pole pieces, contacts the axes of which extend parallel to the axis of the measuring light beam, being supported in the contact carrier for holding a transversely heated furnace for the electrothermal atomization of the sample in the air gap of the solenoid and for the current supply to this furnace.

2. Atomic absorption spectrometer as set forth in claim 1, further comprising coil holders disposed on said pole pieces and field coils for generating the magnetic field arranged on said coil holders.

3. Atomic absorption spectrometer as set forth in claim 2 wherein the contact carrier is integral with said coil holders which carry the field coils and is attached to both pole pieces with the coil holder.

4. Atomic absorption spectrometer as set forth in claim 2, wherein
   (a) in addition to a line emitting first light source generating the measuring light beam a second light source emitting a continuum is provided for background compensation and is switched on alternately with the line emitting first light source, and
   (b) a beam splitter is optionally movable into the path of rays and is arranged such that a measuring light beam originating from the second light source is reflected into the path of rays of the measuring light beam originating from the first light source.

5. Atomic absorption spectrometer as set forth in claim 4, wherein the change between first and second light sources is effected at a frequency higher than 500 cycles per second.

* * * * *